United States Patent [19]

Chibata et al.

[11] 4,350,765

[45] Sep. 21, 1982

[54] METHOD FOR PRODUCING ETHANOL WITH IMMOBILIZED MICROORGANISM

[75] Inventors: Ichiro Chibata, Suita; Jyoji Kato, Yawata; Mitsuru Wada, Nara, all of Japan

[73] Assignee: Tanabe Seiyaku Co., Ltd., Osaka, Japan

[21] Appl. No.: 156,868

[22] Filed: Jun. 5, 1980

[30] Foreign Application Priority Data

Jun. 13, 1979 [JP] Japan .................................. 54-74972
Sep. 28, 1979 [JP] Japan ................................ 54-125966

[51] Int. Cl.$^3$ ..................... C12P 7/06; C12N 11/10; C12N 11/04
[52] U.S. Cl. ..................................... 435/161; 426/11; 435/162; 435/178; 435/182
[58] Field of Search ................... 426/11, 16; 435/161, 435/245, 174, 177, 178, 179, 182, 162

[56] References Cited

U.S. PATENT DOCUMENTS

1,974,937  9/1934  White ............................. 435/245 X
4,138,292  2/1979  Chibata et al. ....................... 435/178

FOREIGN PATENT DOCUMENTS

54-135295 10/1979 Japan .

OTHER PUBLICATIONS

Kierstan et al., The Immobilization of Microbial Cells, Subcellular Organelles, and Enzymes in Calcium Alginate Gels, Biotech. & Bioeng., vol. XIX, 1977 (pp. 387-397).

Cysemski et al., Rapid Ethanol Fermentations Using Vacuum and Cell Recycle, Biotech. & Bioeng., vol. XIX, 1977, (pp. 1125-1143).

Chibata et al., Transformations of Organic Compounds by Immobilized Microbial Cells, Advances in Applied Microbiology, vol. XXII, 1977 (pp. 1-27).

*Primary Examiner*—David M. Naff
*Attorney, Agent, or Firm*—Bierman & Bierman

[57] ABSTRACT

Ethanol is produced in high concentration of 75 mg/ml or above such as 200 mg/ml by using an immbolized ethanol-producing microorganism to convert sugar to ethanol in a nutrient culture broth containing not more than 100 mg/ml sugar until the concentration of sugar is not more than 20% of its initial concentration, then adding a fresh culture broth containing not less than 100 mg/ml sugar and converting sugar to ethanol with the immobilized microorganism to produce the desired high concentration of ethanol. The microorganism is preferably immobilized in a sulfated polysaccharide gel as a dense layer near the surface of the gel.

11 Claims, 3 Drawing Figures

FIG.2
FIG.3
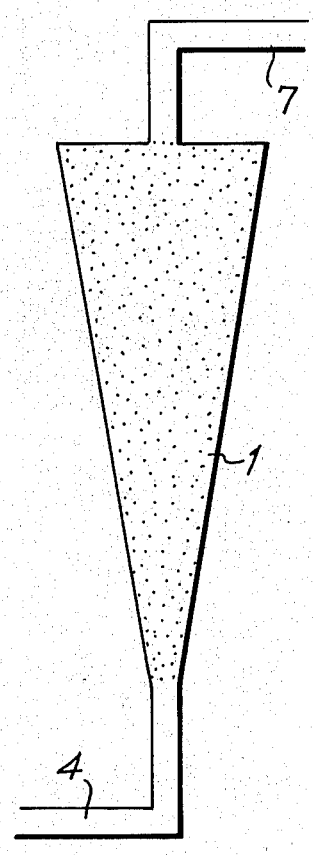
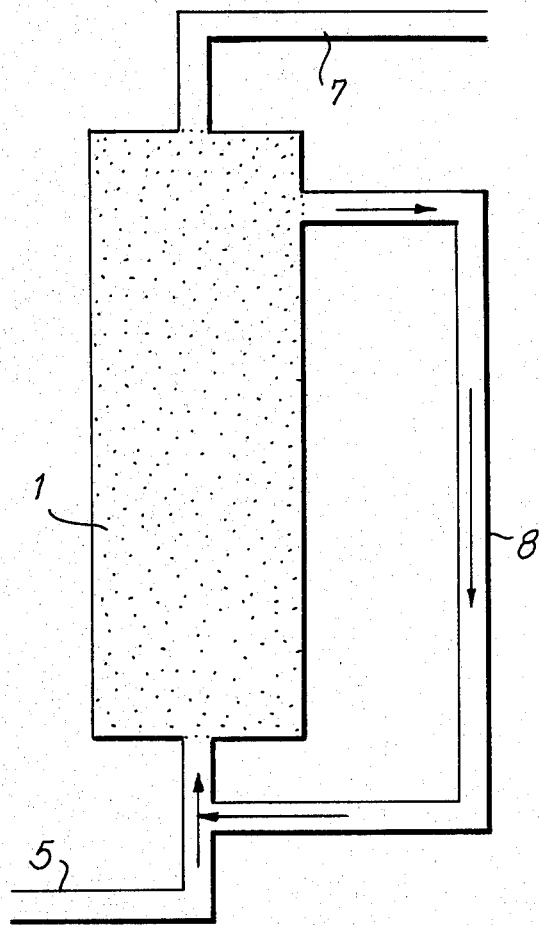

METHOD FOR PRODUCING ETHANOL WITH IMMOBILIZED MICROORGANISM

The present invention relates to a method for producing ethanol in a high concentration by using a yeast or an anaerobe having ethanol-producing activity which is immobilized in supporting gels (hereinafter referred to as an immobilized microorganism). More particularly, the method of the present invention involves the steps of contacting an immobilized microorganism with a culture broth containing a fermentative sugar as a source of ethanol and nutrients other than a fermentative sugar necessitated for growth of the microorganism, microbiologically converting the sugar into ethanol and, then, separating the broth containing ethanol thus produced in a high concentration.

From ancient times, ethanol has been produced by a yeast-fermentation method. Although, in a conventional yeast-fermentation method, a culture broth containing ethanol in the concentration of 50 to 70 mg/ml can be obtained after fermentation for 20 to 40 hours, it takes more than 1 month to produce ethanol in a high concentration such as 200 mg/ml. Moreover, a conventional yeast-fermentation method is economically disadvantageous since the method is carried out by a batch process and it requires a great deal of work and expense in order to recover and re-use yeast cells after completion of fermentation in a batch process.

Recently, it has been proposed that a certain useful materials can be produced by utilizing a complex enzyme system of an immobilized microorganism in a conversion reaction of a suitable substrate into the desired material. For example, it is reported that a complex enzyme system of an immobilized yeast which is prepared by immobilization of yeast cells in calcium alginate gels can be utilized in the production of ethanol from glucose (*Biotechnology and Bioengineering*, Vol. 19, pages 387 to 397 (1977)).

According to the above method, a conversion reaction of glucose into ethanol is carried out by contacting an immobilized yeast with a solution containing glucose and calcium chloride. However, the productivity of this method is low since ethanol-producing activity of the immobilized yeast is low and concentration of ethanol produced is at most about 50 mg per ml of the reaction mixture even at the end of a long-time conversion reaction. Further, the method has such the defect that the enzyme activity is rapidly lowered with the lapse of reaction time, since nutrients other than glucose necessitated for growth of the yeast are not used in the reaction.

The present inventors have previously developed a novel process for preparing an immobilized microorganism (Japanese Patent Publication (unexamined) No. 135295/1979). According to this process, a dense layer of microbial cells is formed within a supporting gel and, in ethanol production, the dense layer of yeast cells immobilized by this process exhibits an ethanol-producing activity more than ten times as high as that of a culture broth obtained by conventional yeast-fermentation. For example, 50 mg/ml of ethanol are produced by contacting 100 mg/ml of a fermentative sugar with the immobilized yeast (one ml of the gel) for one hour. However, the ethanol-producing yeast or anaerobe immobilized by this known method is still unsatisfactory for use in an industrial scale production of ethanol, because the ethanol-producing activity of said immobilized microorganism is restrained remarkably when a fermentative sugar is used in a concentration higher than 150 mg/ml. For example, the immobilized microorganism when contacted with 200 mg/ml of the fermentative sugar shows only 30% of its intrinsic activity, whereas said immobilized microorganism usually exhibits the full ethanol-producing activity in the presence of less than 100 mg/ml of the fermentative sugar. Thus, if the conversion reaction of a fermentative sugar to ethanol is conducted according to the known method by the use of the immobilized microorganism, the fermentative sugar must be used at a concentration of less than 100 mg/ml and the concentration of ethanol to be produced must be not more than 50 mg/ml, because otherwise the sugar induces remarkable decrease in the ethanol-productivity of the immobilized microorganism.

The present inventors have newly found that an immobilized microorganism exhibits a superior activity over a long period of time and ethanol can be produced in a high concentration such as about 100–200 mg/ml within a relatively short time, when the conversion reaction of a fermentative sugar into ethanol is carried out by contacting an immobilized microorganism with a culture broth containing a fermentative sugar in a relatively low concentration as well as nutrients other than the fermentative sugar necessitated for growth of the microorganism, and, subsequently, repeating the addition of a fresh culture broth containing the sugar in a relatively high concentration, preferably, together with the other nutrients.

One object of the present invention is to provide a method for producing ethanol in a high concentration by using an immobilized microorganism. Another object of the present invention is to provide a method for producing ethanol in a high concentration in a short period of time.

These objects as well as other objects and advantages of the present invention will become apparent to those skilled in the art from the following description by reference to the accompanying drawings wherein:

FIG. 2 is a schematic flow chart showing another embodiment of the present invention by using an inverse conical columnar reaction equipment; and FIG. 3 is a schematic flow chart showing still another embodiment of the present invention by using a cylindrical columnar reaction equipment having a circulating tube.

Figure 1:
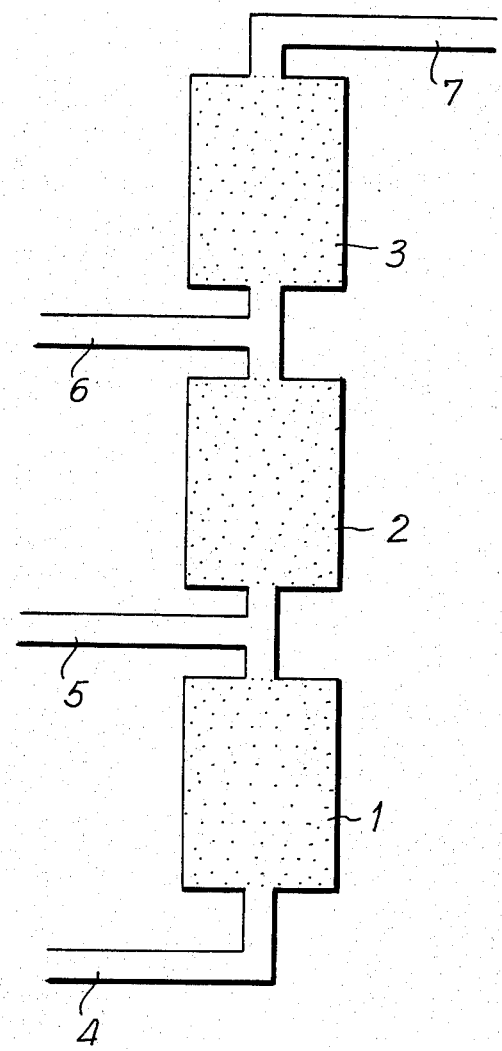
FIG. 1 is a schematic flow chart showing an embodiment of the present invention by using a series of cylindrical columnar reaction equipments.

According to the present invention, there is provided a method of producing ethanol in a high concentration by using an immobilized microorganism, which comprises contacting the immobilized cells of an ethanol-producing yeast or anaerobe (said yeast or anaerobe being selected from the group consisting of the genera of *Saccharomyces* and *Zymomonas*) with a nutrient culture broth containing a fermentative sugar to convert said sugar into ethanol. In particular, the conversion reaction of the present invention can be preferably carried out by the steps of:

(1) contacting said immobilized microorganism with a culture broth containing a fermentative sugar and other nutrients necessitated for growth of the microorganism;

(2) microbiologically converting the sugar into ethanol;

(3) adding an additional fresh culture broth containing the sugar to the conversion reaction system; and then (4) separating the broth containing ethanol produced.

More specifically, for example, a broth containing ethanol in a concentration as high as about 100 to 200 mg/ml can be stably obtained in much shorter period of time in comparison with a converntional yeast-fermentation method by initially contacting the immobilized ethanol-producing microorganism with a culture broth containing a fermentative sugar, preferably, in a relatively low concentration such as 50–100 mg/ml, together with nutrients other than the fermentative sugar necessitated for growth of the microorganism; microbiologically converting the sugar into ethanol until the sugar concentration in the broth is lowered to not more than 20% of its initial concentration; and then adding an additional fresh culture broth containing not less than 100 mg/ml of the sugar to the conversion reaction system until ethanol is produced in a concentration of not less than 75 mg/ml, or more preferably until ethanol is produced in a concentration of not less than 100 mg/ml.

A microorganism to be used in the present invention is a yeast or an anaerobe having ethanol-producing activity and such microorganism is selected from the group consisting of the genera of Saccharomyces and Zymomonas. Examples of these microorganisms are a brewer's yeast such as Sacch. cerevisiae IFO 2018 and Sacch. uvarum IFO 1167; a distillery yeast such as Sacch. cerevisiae IFO 0216, Sacch. cerevisiae IFO 0233, Sacch. cerevisiae ATCC 4111 and Sacc. cerevisiae ATCC 4124; a sake yeast such as Sacch. sake ATCC 26422 (Japan strain Kyokai 7); a wine yeast such as Sacc. cerevisiae IFO 1661, Sacch. cerevisiae ATCC 4098 and Sacch. cerevisiae ATCC 4921; Sacch. carlsbergensis OUT 7013; Sacch. pasterianus OUT 7122; Sacch. fermentati IFO 0422; Zymomonas mobilis IFO 13756; Zymomonas anaerobea ATCC 29501 and the like. All of these microorganisms mentioned above are well known to the art and are freely available to the public.

Any one of the above-mentioned yeast or anaerobe immobilized in supporting gels may be used in the present invention, and the immobilization of said microorganism can be effected by a known method, for example, a sulfated polysaccharide-gel method (U.S. Pat. No. 4,138,292), a polyacrylamide-gel method (Advances in Applied Microbiology, Vol. 22. Pages 1 (1977)) and the like. In the present invention, the immobilization can also be effected according to the process disclosed in Japanese Patent Publication (unexamined) No. 135295/1979. For example, a small amount of microbial cells are mixed with a solution of a gel base material and the resulting mixture is gelatinized in pellets or film according to a known gelation method, for example, the mixture is added dropwise into a solution of a gelatinizer, to obtain pallets or film of 2 mm to 5 mm in thickness containing 0.01 to 10 loopful of microbial cells per 100 g (wet weight) of gels. The gels are, then, incubated in a nutrient culture broth suitable for growth of the microorganism at 15° to 45° C. to obtain a desired immobilized microorganism which has a dense layer of the microbial cells formed within the supporting gel near the surface of the gel. As a gel base material, there can be used a known gel base material such as sulfated polysaccharide, polyacrylamide (e.g., 2-methyl-5-vinylpridine-methyl-methacrylate-methacrylic acid copolymer), sodium alginate, polyvinylalcohol, cellulose succinate, casein succinate and the like. Any one of the sulfated polysaccharide which contains not less than 10 w/w %, preferably 12 to 62 w/w %, of sulfate ($-SO_3H$) moiety in its molecule can be used as the above-mentioned sulfated polysaccharide, and examples of such sulfated polysaccharide include carrageenan, furcellaran and cellulose sulfate. Carrageenan contains about 20–30 w/w % of sulfate ($SO_3H$) moiety in the molecule. On the other hand, furcellaran contains about 12 to 16 w/w % of sulfate moiety in its molecule. Cellulose sulfate containing 12 to 62 w/w % of sulfate moiety in the molecule is available in the market under the trade name "KELCO SCS" (KELCO Co., U.S.A.) (sulfate content: about 53%) or, if required, may be prepared by conventional esterification of cellulose with sulfuric acid.

In carrying out the method of the present invention, firstly, a nutrient broth is prepared by mixing in water a source of nitrogen such as a yeast extract, a corn steep liquor, a peptone or the like and one or plurality of other nutrients necessitated for growth of a microorganism to be used. Such other nutrients may be selected from vitamins such as thiamine, biotin, pantothenic acid, inositol or the like; minerals such as phosphates, magnesium salts, calcium salts, sodium salts, potassium salts or the like; ammonium salts such as ammonium chloride; and a mixture thereof. The amount of these nutrients to be added will be apparent to those skilled in the art and, for example, 0.05 to 1.0 w/v % of a nitrogen source, 0.0001 to 0.1 w/v % of a mineral, 0.01 to 1.0 w/v % of an ammonium salt and a trace amount of vitamines can be added to a nutrient broth. Then, a fermentative sugar such as glucose, fructose, sucrose, maltose or the like is added to the nutrient broth thus produced, preferably, in a relatively low concentration such as not more than about 10 w/v % (i.e., not more than about 100 mg/ml), preferably 5 to 10 w/v % (i.e., about 50 to 100 mg/ml), based on the nutrient broth to obtain a culture broth. Molasses contains both the fermentative sugar and other nutrients necessitated for growth of the microorganism. Therefore, an aqueous molasses solution per se can be used as the culture broth.

The method of the present invention can be carried out according to either a batch process or a continuous process using a columnar reaction equipment at a temperature of 15° to 45° C. suitable for growth of an immobilized microorganism to be used.

In case of carrying out the method according to a batch process, the immobilized microorganism is first contacted with a culture broth with stirring to convert a fermentative sugar in the broth into ethanol. When the concentration of the sugar is lowered to, for example, not more than about 20% of the initial concentration, preferably, not more than about 10 mg/ml, an additional fresh culture broth containing the sugar is added to the conversion reaction system. Likewise above, the sugar newly added is also converted into ethanol and the concentration of the sugar in the broth is again lowered. If required, the addition of a fresh culture broth containing the sugar may be repeated intermittently until ethanol is produced in a high concentration such as 100 mg/ml to 200 mg/ml. The additional fresh culture broth to be added to the conversion reaction system should contain a fermentative sugar in a relatively high concentration such as not less than about 100 mg/ml, preferably, together with nutrients other than the fermentative sugar necessitated for growth of an immobilized microorganism and each time when an additional broth is added, the concentration of the sugar in the broth to be added may be intermittently increased up to about 250-400 mg/ml. It is preferred that the addition of a fresh culture broth containing not less than 100 mg/ml of the sugar is repeated when the concentration of the sugar in the conversion reaction system is lowered to not more than about 20% of its initial concentration.

In case of carrying out the method according to a continuous process, a columnar reaction equipment packed with an immobilized microorganism is used. Firstly, a culture broth containing not more than 100 mg/ml, more preferably 50 to 100 mg/ml, of a fermentative sugar together with nutrients other than the fermentative sugar necessitated for growth of the microorganism is fed through one end of the column to convert the sugar into ethanol and a broth containing ethanol thus produced is flowed out through the other end of the column. The feed rate of the above-mentioned culture broth should be adjusted so that the concentration of the sugar in the effluent from the column is not more than about 20% of its initial concentration, preferably not more than about 10 mg/ml. Thereafter, an additional culture broth containing not less than 100 mg/ml of the sugar is fed to the column and, in this case, it is especially preferred to adjust the feed rate of said fresh culture broth so that the concentration of the sugar in an effluent becomes not more than 20% of its initial concentration. In addition, the concentration of the sugar in a culture broth to be continuously fed to the column may be gradually increased up to about 250 to 400 mg/ml with the lapse of time. When the above process is carried out, an immobilized microorganism maintains an excellent ethanol-productivity over a long period of time, and ethanol can be produced in a high concentration such as at most about 200 mg/ml.

Further, a series of columns can be used in the above continuous process by adjusting the feed rate of the initial culture broth so that the concentration of the sugar in an effluent from the first column is lowered to not more than about 20% of the initial concentration, preferably, not more than about 10 mg/ml, feeding an additional culture broth containing the sugar to the second column together with the effluent from the first column, and then, repeating this feeding procedure in the subsequent columns. A long column can also be used by adjusting the feed rate of the initial culture broth so that the concentration of the sugar at a certain part of a column is lowered to not more than about 20% of the initial concentration, feeding an additional culture broth containing sugar to the part of the column where the sugar concentration is lowered, and then, repeating this feeding procedure at the subsequent parts of the column. As a matter of course, these latter processes can increase the output of ethanol per unit time and ethanol can be produced quite efficiently and continuously in a high concentration.

The separation of a broth after completion of the conversion reaction can be effected by conventional methods such as distillation, centrifugation, decantation and the like. In case of using a column, a broth can readily be separated as an effluent from the column.

The following examples further illustrate the present incention in detail but are not to be construed to limit the scope thereof. In the examples, ethanol-producing activity of an immobilized microorganism is determined from the amount of ethanol produced. Further, it should be noted that the concentration of a fermentative sugar described in the specification and claims has been expressed by calculating it as that of glucose.

EXAMPLE 1

One loopful of *Sacch. sake* ATCC 26422 (Japan strain Kyokai 7) was admixed with a sterilized 4.5 w/v % aqueous solution of carrageenan (manufactured by The Copenhagen Pectin Factory Ltd., under the trade name "GENUGEL Type WG") (20 ml) at 37° C. The mixture was added dropwise from a nozzle to a 2 w/v % aqueous solution of potassium chloride (200 ml) to obtain globular gels of 4 mm in diameter.

A nutrient broth was prepared by admixing a yeast extract (0.15 w/v %), ammonium chloride (0.25 w/v %), dipotassium hydrogenphosphate (0.55 w/v %), magnesium sulfate heptahydrate (0.025 w/v %), calcium chloride (0.001 w/v %), citric acid (0.1 w/v %) and sodium chloride (0.25 w/v %) in water and adjusting the pH thereof to 5.0.

Glucose was added to the above obtained gels at the concentration of 10 w/v % and the above obtained gels were incubated in the glucose-containing broth (500 ml) with gentle shaking at 30° C. for 60 hours to grow the yeast in the gels. The immobilized yeast thus obtained had 50 mg ethanol/ml of the gels/hr of ethanol-producing activity.

The immobilized yeast (20 ml) was contacted with the nutrient broth containing 10 w/v % of glucose (20 ml) at 30° C. for 1 hour. When the concentration of the remaining glucose in the broth was lowered to 2 mg/ml, the additional fresh nutrient broth containing 40 w/v % of glucose (10 ml) was added and the conversion reaction of glucose into ethanol was continued under the same condition. As the result, the broth containing ethanol in the concentration of 100 mg/ml (30 ml) was obtained after the conversion reaction for 3 hours.

EXAMPLE 2

According to the same procedure as described in Example 1, an immobilized yeast was obtained. The immobilized yeast (20 ml) was contacted with a nutrient broth (the same as in Example 1) containing 10 w/v % of glucose (20 ml) at 30° C. for 1 hour. When the concentration of the remaining glucose in the broth was lowered to 2 mg/ml, the additional fresh nutrient broth containing 40 w/v % of glucose (5 ml) was added and the conversion reaction of glucose into ethanol was continued for another 1 hour under the same condition. Thereafter, the addition of the nutrient broth containing 40 w/v % of glucose (5 ml) was repeated 3 times at an hour-intervals. As a result, the immobilized yeast kept its ethanol-producing activity at the level of 50 mg/ml of the gels/hr during the reaction period and the broth containing ethanol in a concentration of 125 mg/ml (40 ml) was obtained after the conversion reaction for 5 hours.

EXAMPLE 3

After carrying out the same procedure as described in Example 2, the immobilized yeast was recovered by decantation. The same procedure as described in Example 2 was repeated by using the recovered immobilized yeast to produce ethanol. The ethanol-producing activity of the recovered immobilized yeast was not lowered even after the recovery and the production of ethanol were repeated 10 times and the broth containing ethanol in a concentration of 125 mg/ml (40 ml) was obtained at the end of every conversion reaction for 5 hours.

EXAMPLE 4

An immobilized yeast (20 ml) prepared according to the same procedure as described in Example 1 was packed in a cylindrical column (volume: 30 ml). A nutrient broth (the same as in Example 1) containing 10 w/v % of glucose was fed to the column through one end thereof at the rate of 20 ml/hr at 30° C. to float the immobilized yeast and flowed out from the column through the other end thereof at the same rate. After incubation at 30° C. for 60 hours while feeding the broth at the above feed rate, the feed rate was adjusted to 7 ml/hr to flow out the effluent containing glucose in the concentration of not more than 10 mg/ml. Under this condition, glucose concentration in the nutrient broth to be fed to the column was gradually increased so that glucose concentration thereof reached 30 w/v % based on the broth after 120 hours. During this peiod, ethanol-producing activity of the immobilized yeast was not lowered and the effluent containing ethanol in a concentration of 150 mg/ml was obtained. Further, when the nutrient broth containing 30 w/v % of glucose was continuously fed to the column at the rate of 7 ml/hr, the immobilized yeast in the column was still stable for more than 1 month and the effluent containing ethanol in a concentration of 146 mg/ml on an average was constantly obtained.

EXAMPLE 5

Ethanol production was carried out by using a cylindrical columnar reaction equipment as shown in FIG. 1 having a series of three columns 1, 2 and 3. Each column (volume: 30 ml) was prepared according to the same procedure as described in Example 4 by packing an immobilized yeast (the same as Example 1) (20 ml) into the column and feeding the nutrient broth (the same as in Example 1) containing 10 w/v % of glucose at the rate of 20 ml/hr at 30° C. for 60 hours. Then the columns were connected in series. The nutrient broth containing 10 w/v % of glucose was fed to the bottom of column 1 though a feeding pipe 4 at the rate of 20 ml/hr at 30° C. The effluent from column 1 was led to column 2 together with the nutrient broth containing 40 w/v % of glucose which was fed through a broth feeding pipe 5 at the rate of 5 ml/hr. Likewise, the effluent from column 2 was led to column 3 together with the nutrient broth containing 40 w/v % of glucose fed through a broth feeding pipe 6 at the rate of 5 ml/hr. Thus, the effluent containing ethanol in a concentration of 100 mg/ml was constantly obtained from column 3 through an outlet pipe 7 at the rate of 30 ml/hr.

EXAMPLE 6

In the same procedure as described in Example 4, 20 w/v % of an aqueous molasses solution was substituted for 10 w/v % of glucose in the initial nutrient broth (100 mg/ml as glucose) and the concentration of the aqueous molasses in the additional nutrient broth was gradually increased up to 60 w/v % to continuously obtain the effluent containing ethanol in a concentration of 142 mg/ml at the rate of 5 ml/hr.

EXAMPLE 7

Ethanol production was carried out by using an inverse conical columnar reaction equipment as shown in FIG. 2. An inverse conical column 1 (volume: 30 ml) was prepared by packing into the column an immobilized yeast (20 ml) obtained by the same procedure as described in Example 1, feeding a nutrient broth (the same as in Example 1) containing 10 w/v % of glucose to the bottom of column 1 through a broth feeding pipe 4 at the rate of 20 ml/hr at 30° C. and flowing out the broth from the top of column 1 through an outlet pipe 7 at the same rate. After incubation at 30° C. for 40 hours while feeding the broth at the above feed rate, the feed rate was adjusted to 6 ml/hr to flow out the effluent containing glucose in a concentration of not more than 10 mg/ml. Under this condition, glucose concentration in the nutrient broth to be fed to the column was gradually increased so that glucose concentration thereof reached to 35 w/v % based on the broth after 72 hours. During this period, ethanol-producing activity of the immobilized yeast was not lowered and the effluent containing ethanol in a concentration of 175 mg/ml was constantly obtained. Thus, when the inverse conical column is used, ethanol can be efficiently produced since $CO_2$ gas formed in a conversion reaction of a fermentative sugar into ethanol can be efficiently removed.

EXAMPLE 8

Ethanol production was carried out by using a cylindrical columnar reaction equipment having a circulating tube as shown in FIG. 3. A column 1 having a circulating tube 8 which being able to circulate a portion of a broth flowed through column 1 to the bottom of the column was prepared by packing an immobilized yeast (25 ml) obtained by the same procedure as described in Example 1 into the colume, feeding 20 w/v % of an aqueous molasses solution (100 mg/ml as glucose) to the bottom of column 1 through a broth feeding pipe 5 at the rate of 25 ml/hr at 30° C. to float the immobilized yeast in the column and flowing out the broth from the top of the column through an outlet pipe 7 at the same rate. After incubation at 30° C. for 40 hours while feeding the broth at the above feed rate, 50 w/v % of the aqueous molasses solution (250 mg/ml as glucose) was fed to column 1 at the rate of 10 ml/hr while a portion of the broth flowed through the column was circulated to the bottom of the column through the tube 8 at the rate of 100 ml/hr. The concentration of the aqueous molasses circulating through the tube 8 lowered to not more than 10 mg/ml as glucose. Under this condition, ethanol-producing activity of the immobilized yeast was not lowered and the effluent containing ethanol in the concentration of 125 mg/ml was continuously flowed out from the pipe 7, since the concentration of the aqueous molasses in the broth to be fed to the column was diluted with the circulated broth through the tube 8.

EXAMPLE 9

One loopful of *Zymomonas mobils* IFO 13756 was admixed with a sterilized 4.5 w/v % aqueous carageenan solution (20 ml) at 37° C. The mixture was added dropwise from a nozzle to a 2 w/v % aqueous potassium chloride solution (200 ml) to obtain globular gels of 4 mm in diameter.

A nutrient broth was prepared by admixing yeast extract (0.15 w/v %), ammonium chloride (0.25 w/v %), dipotassium hydrogenphosphate (0.55 w/v %), magnesium sulfate heptahydrate (0.025 w/v %), calcium chloride (0.001 w/v %), citric acid (0.1 w/v %) and sodium chloride (0.25 w/v %) in water and adjusted the pH thereof to 6.8.

Glucose was added to the nutrient broth in the concentration of 10 w/v % and the above-obtained gels were incubated in the glucose-containing broth (500 ml) at 30° C. for 90 hours under nitrogen to grow the anaerobe in the gels. The immobilized anaerobe thus obtained had 77 mg ethanol/ml of the gels/hr of ethanol-producing activity.

The immobilized anaerobe (20 ml) was contacted with the nutrient broth containing 10 w/v % of glucose (20 ml) at 30° C. for 45 minutes. When the concentration of the remaining glucose in the broth was lowered to 2 mg/ml, the additional fresh nutrient broth containing 40 w/v % of glucose (10 ml) was added and the conversion reaction of glucose into ethanol was continued under the same condition. As the result, the broth containing ethanol in the concentration of 100 mg/ml (30 ml) was obtained after the conversion reaction for 2 hours without lowering of the activity of the immobilized anaerobe.

EXAMPLE 10

According to the same procedure as described in Example 9, an immobilized anaerobe was obtained. The immobilized anaerobe (20 ml) was contacted with a nutrient broth (the same as Example 9) containing 10 w/v % of glucose (20 ml) at 30° C. for 40 minutes. When the concentration of the remaining glucose in the broth was lowered to 2 mg/ml, the additional fresh nutrient broth containing 40 w/v % of glucose (5 ml) was added and the conversion reaction of glucose into ethanol was continued for another 40 minutes under the same condition. Thereafter, the addition of the nutrient broth containing 40 w/v % of glucose (5 ml) was repeated 3 times at 40-minute intervals. As the result, the immobilized anaerobe kept its ethanol-producing activity at the level of 77 mg ethanol/ml of the gels/hr and the broth containing ethanol in a concentration of 125 mg/ml (40 ml) was obtained after the conversion reaction for 200 minutes.

EXAMPLE 11

After carrying out the same procedure as described in Example 10, the immobilized anaerobe was recovered by decantation. The same procedure as described in Example 10 was repeated by using the recovered immobilized anaerobe to produce ethanol. The ethanol-producing activity of the recovered immobilized anaerobe was not lowered even after the recovery and the production of ethanol were repeated 10 times and the broth containing ethanol in the concentration of 125 mg/ml (40 ml) was obtained at the end of every conversion reaction for 200 minutes.

EXAMPLE 12

According to the same procedure as described in Example 5, ethanol production was carried out by using a cylindrical columnar reaction equipment as shown in FIG. 1. Each column (volume: 30 ml) was prepared by packing an immobilized anaerobe (the same as in Example 9) (20 ml) into the column and feeding a nutrient broth (the same as in Example 9) containing 10 w/v % of glucose at the rate of 30 ml/hr at 30° C. for 90 hours. Then, columns 1, 2 and 3 were connected in series. The nutrient broth containing 10 w/v % of glucose was fed to the bottom of column 1 through a broth feeding pipe 4 at the rate of 30 ml/hr at 30° C. The effluent from column 1 was led to column 2 together with the nutrient broth containing 40 w/v % of glucose fed through a pipe 5 at the rate of 7 ml/hr. Likewise, the effluent from column 2 was led to column 3 together with the nutrient broth containing 40 w/v % of glucose fed through a pipe 6 at the rate of 7 ml/hr. Thus, the effluent containing ethanol in a concentration of 100 mg/ml was continuously flowed out from column 3 through an outlet pipe 7 at rate of 44 ml/hr.

EXAMPLE 13

In the same procedure as described in Example 10, 20 w/v % of an aqueous molasses solution was substituted for glucose in the initial nutrient broth (100 mg/ml as glucose) and the concentration of the aqueous molasses was gradually increased up to 60 w/v % to obtain the broth containing ethanol in a concentration of 125 mg/ml (40 ml) after the conversion reaction of the aqueous molasses into ethanol for 3 hours.

EXAMPLE 14

According to the same procedure as described in Example 8, ethanol production was carried out by using a cylindrical columnar reaction equipment having a circulating tube as shown in FIG. 3. A column 1 was prepared by packing into the column an immobilized anaerobe (25 ml) obtained by the same procedure as described in Example 9, feeding 20 w/v & of an aqueous molasses solution of (100 mg/ml as glucose) to the bottom of column 1 through a pipe 5 at the rate of 40 mg/hr at 30° C. for 90 hours and flowing out from the top of the column through an outlet pipe 7 at the same rate. Then, the 50 w/v % of the molasses solution (250 mg/ml as glucose) was fed to column 1 at the rate of 15 ml/hr while a portion of the broth flowed through the column was circulated to the bottom of the column through the circulating tube 8 at the rate of 100 ml/hr. The concentration of the aqueous molasses circulating through the tube 8 lowered to not more than 10 mg/ml as glucose. Under this condition, ethanol-producing activity of the immobilized anaerobe was not lowered and the effluent containing ethanol in a concentration of 125 mg/ml was continuously flowed out from the pipe 7, since the concentration of the aqueous molasses to be fed to the column was diluted with the circulated broth through the tube 8.

What we claim is:
1. A method for producing ethanol by conversion reaction of fermentative sugar into ethanol, which comprises the steps of:
  (1) contacting an ethanol-producing microorganism immobilized in a sulfated polysaccharide gel containing not less than 10 w/w % of sulfate ($-SO_3H$) moiety with a nutrient culture broth containing not more than 100 mg/ml of a fermentative sugar, said ethanol-producing microorganism being selected from the group consisting of the genera of Saccharomyces and Zymomonas and said microorganism being immobilized in said sulfated polysaccharide gel as a dense layer near the surface of said gel,
  (2) microbiologically converting said sugar into ethanol until the concentration of the sugar in the broth is lowered to not more than 20% of its initial concentration;
  (3) contacting the broth from step (2) and said immobilized microorganism with additional fresh culture broth containing not less than 100 mg/ml of the sugar until ethanol is produced in a concentration in the broth of not less than 75 mg/ml; and then

(4) separating the broth containing the ethanol produced.

2. The method of claim 1 wherein said nutrient culture broth contains at least 50 mg/ml of said sugar.

3. A method for producing ethanol according to claim 2, wherein the sulfated polysaccharide is carrageenan, furcellaran or cellulose sulfate.

4. A method for producing ethanol according to claim 2, wherein said addition of the fresh culture broth containing the sugar is conducted until ethanol is produced in a concentration of not less than 100 mg/ml.

5. A method for producing ethanol according to claim 2, wherein said addition of the fresh culture broth containing the sugar is repeated intermittently or continuously.

6. A method for producing ethanol according to claim 2, wherein said fresh culture broth containing the sugar is added so that the sugar concentration in the broth in which ethanol is being produced is adjusted to 100–400 mg/ml.

7. A method for producing ethanol according to claim 2, wherein the method is carried out by a batch process.

8. A method for producing ethanol according to claim 7, wherein the addition of the fresh culture broth is repeated when the concentration of the sugar in the broth in which ethanol is being produced is lowered to not more than 20% of its initial concentration.

9. A method for producing ethanol according to claim 2, wherein the method is carried out by a continuous process using one or plurality of columns packed with said immobilized microorganism.

10. A method for producing ethanol according to claim 9, wherein the addition of the fresh culture broth is continuously repeated by adjusting the feed rate of the broth so that the concentration of the sugar in an affluent is not more than 20% of its initial concentration.

11. A method for producing ethanol according to claim 9, wherein the column is an inverse conical column having a broth feeding pipe at the bottom thereof and an outlet pipe at the top thereof.

* * * * *